(«12») United States Patent
Dierck

(10) Patent No.: US 8,435,259 B2
(45) Date of Patent: May 7, 2013

(54) SURGICAL TOOL ARRANGEMENT AND SURGICAL CUTTING ACCESSORY FOR USE THEREWITH WITH THE TOOL ARRANGEMENT INCLUDING A TOOTHED CUTTING EDGE AND A GENERALLY STRAIGHT CUTTING EDGE

(75) Inventor: Ryon J. Dierck, Kernville, CA (US)

(73) Assignee: Stryker Corporation, Kalamazoo, MI (US)

( * ) Notice: Subject to any disclaimer, the term of this patent is extended or adjusted under 35 U.S.C. 154(b) by 169 days.

(21) Appl. No.: 12/800,456

(22) Filed: May 14, 2010

(65) Prior Publication Data

US 2010/0298855 A1 Nov. 25, 2010

Related U.S. Application Data

(60) Provisional application No. 61/216,557, filed on May 19, 2009.

(51) Int. Cl.
*A61B 17/32* (2006.01)

(52) U.S. Cl.
USPC .......................................................... 606/170

(58) Field of Classification Search ............. 606/79, 606/160, 170, 171, 175, 176, 178, 179, 180; 604/30, 32, 22
See application file for complete search history.

(56) References Cited

U.S. PATENT DOCUMENTS

| 4,646,738 A | 3/1987 | Trott |
| 4,983,179 A | 1/1991 | Sjostrom |
| 5,084,052 A * | 1/1992 | Jacobs ............................ 606/79 |
| 5,492,527 A | 2/1996 | Glowa et al. |
| 5,601,583 A * | 2/1997 | Donahue et al. .............. 606/170 |
| 5,620,447 A | 4/1997 | Smith et al. |
| 5,766,199 A | 6/1998 | Heisler et al. |
| 5,833,692 A | 11/1998 | Cesarini et al. |
| 6,001,116 A | 12/1999 | Heisler et al. |
| 6,312,441 B1 | 11/2001 | Deng |
| 6,620,180 B1 | 9/2003 | Bays et al. |
| 6,827,725 B2 | 12/2004 | Batchelor et al. |
| 7,237,990 B2 * | 7/2007 | Deng ............................. 409/175 |
| 7,803,170 B2 * | 9/2010 | Mitusina ....................... 606/171 |
| 2003/0135151 A1 | 7/2003 | Deng |
| 2004/0092991 A1 * | 5/2004 | Deng ............................. 606/170 |
| 2004/0220602 A1 * | 11/2004 | Deng et al. .................... 606/170 |
| 2006/0212060 A1 * | 9/2006 | Hacker et al. ................. 606/180 |

FOREIGN PATENT DOCUMENTS

WO WO 2006/102124 A2 9/2006

\* cited by examiner

*Primary Examiner* — Tuan V Nguyen
(74) *Attorney, Agent, or Firm* — Flynn, Thiel, Boutell & Tanis, P.C.

(57) ABSTRACT

A surgical tool arrangement for performing endoscopic surgical procedures which includes a powered handpiece and a cutting accessory which detachably connects to the handpiece and incorporates multiple blade configurations or styles into one accessory. The accessory includes a cutting element which rotates within an outer housing element, wherein each element has a cutting window at its distal end, and one of the cutting windows has two sides which have differently configured cutting geometries. One of the cutting windows has a first side with a cutting edge that is toothed and a second side with a cutting edge that is generally straight.

17 Claims, 7 Drawing Sheets

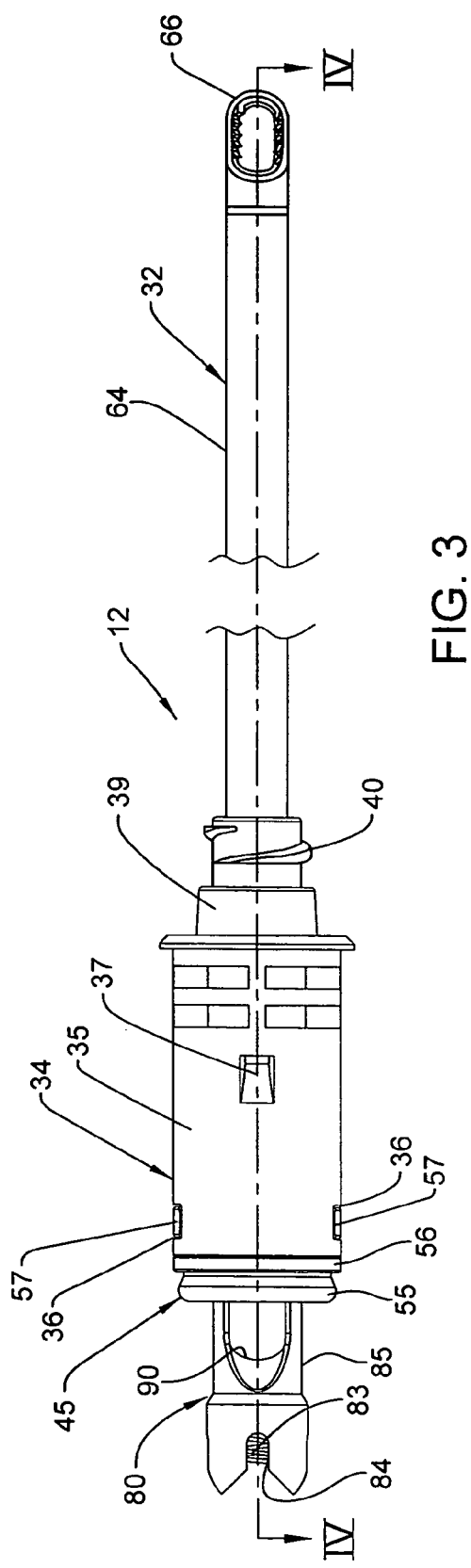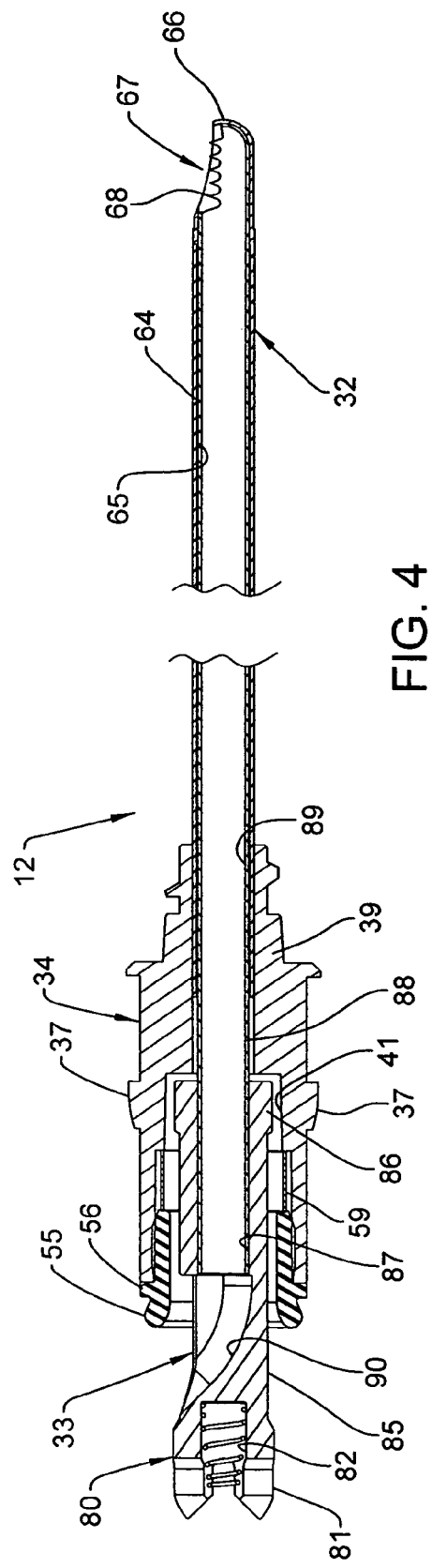

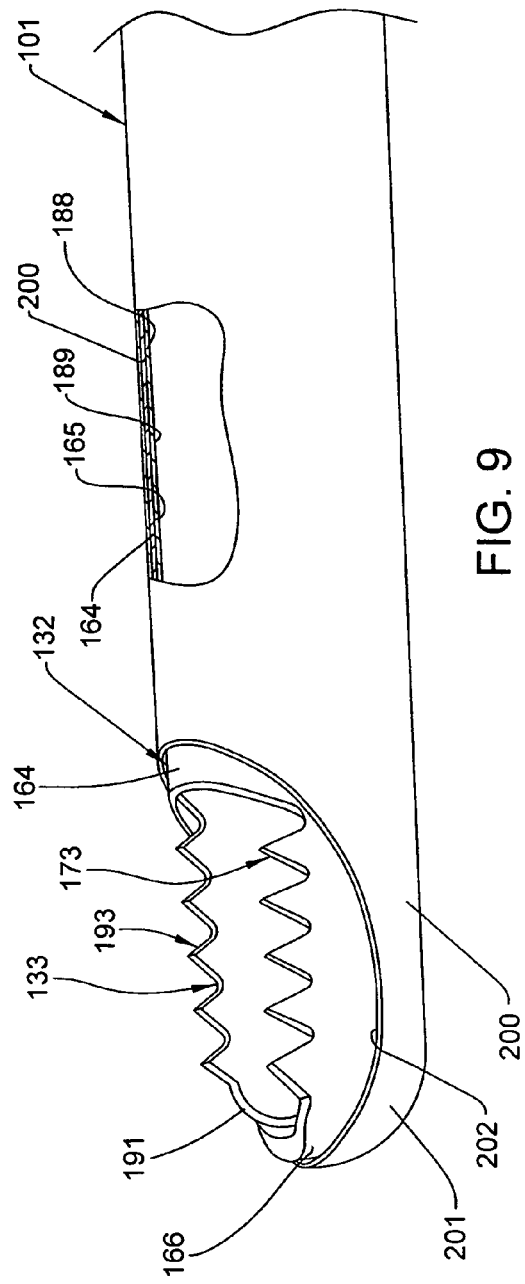
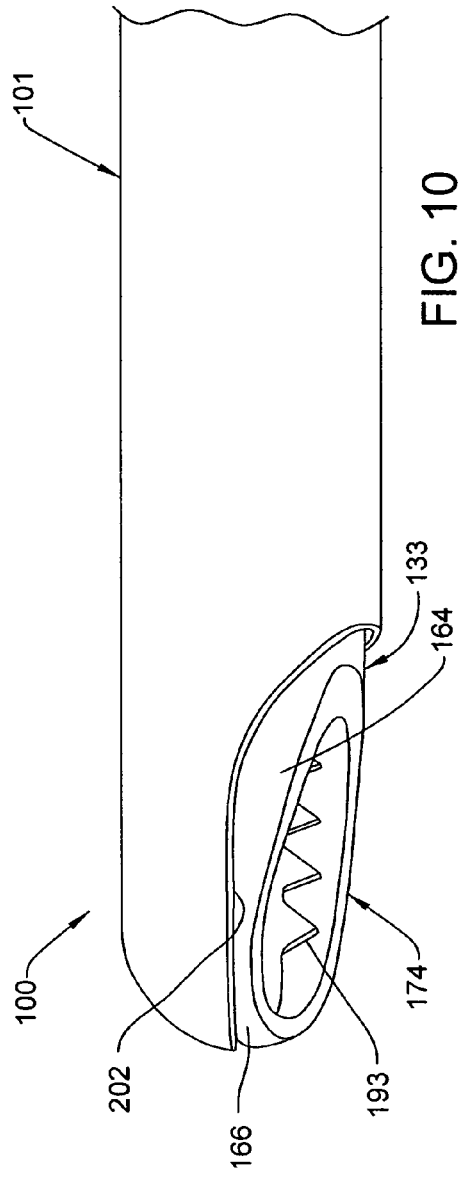

SURGICAL TOOL ARRANGEMENT AND SURGICAL CUTTING ACCESSORY FOR USE THEREWITH WITH THE TOOL ARRANGEMENT INCLUDING A TOOTHED CUTTING EDGE AND A GENERALLY STRAIGHT CUTTING EDGE

CROSS REFERENCE TO RELATED APPLICATION

This application claims the benefit of U.S. Provisional Application Ser. No. 61/216,557, filed May 19, 2009, which is incorporated herein by reference in its entirety.

FIELD OF THE INVENTION

This invention generally relates to a surgical tool arrangement useful for performing endoscopic surgical procedures which includes a powered handpiece and, more particularly, to a cutting accessory which detachably connects to the handpiece and incorporates multiple blade configurations which allow the user to perform multiple cutting styles with one accessory.

BACKGROUND OF THE INVENTION

Endoscopic surgical procedures are routinely performed in order to accomplish various surgical tasks. In such a surgical procedure, small incisions or portals are made in the patient. An endoscope, which is a device that allows medical personnel to view the surgical site, is inserted in one of the portals. Surgical instruments used to perform other tasks are inserted into other portals. The surgeon views the surgical site through the endoscope to determine how to manipulate the surgical instruments in order to accomplish the desired procedure. An advantage of performing endoscopic surgery is that, since the portions of the body that are cut open are minimized, the portions of the body that need to heal after the surgery are likewise reduced. Moreover, during an endoscopic surgical procedure, only relatively small portions of the patient's internal organs and tissue are exposed to the open environment. This minimal opening of the patient's body lessens the extent to which a patient's organs and tissue are open to infection.

The ability to perform endoscopic surgery is enhanced by the development of powered surgical tools especially designed to perform such procedures. Once such tool is sold by the Assignee hereof under the trademark FORMULA®. This tool is in the form of a cylindrical handpiece designed to be held in the hand of the surgeon. The handpiece has a front or distal end provided with a coupling assembly for releasably holding a cutting accessory, and a motor disposed within a handpiece housing which drives the accessory. One such cutting accessory, often termed a "shaver", includes a hub which defines the proximal end of the accessory and is appropriately configured to cooperate with the coupling assembly of the handpiece to lock the accessory thereto, an elongated and tubular housing element having a proximal end fixed to the hub, and an elongated cutting element including a drive shaft disposed within the housing element. When the accessory is attached to the handpiece, the handpiece motor couples to the drive shaft of the accessory and moves same relative to the outer housing element. The handpiece motor is selectively actuable to drive the accessory drive shaft so as to cause a desired cutting action at the distal end of the accessory. The handpiece is associated with a control unit which controls the functioning thereof, and is actuated by the user via appropriate buttons provided on the handpiece itself, or alternatively directly at the control unit.

In an endoscopic surgical procedure, irrigating fluid is introduced into the surgical site. This fluid serves as a transport media for removing tissue and debris from the surgical site. In order to remove the irrigating fluid and the material contained therein, the above handpiece and the various accessories which are usable therewith together define a suction conduit. A suction pump is connected to the handpiece to provide the suction force needed for drawing the fluid and material away from the surgical site. In order to control the suction flow through the accessory and the handpiece, the handpiece is provided with a manually operated valve which is manipulated by the surgeon to control suction of material away from the surgical site.

Mechanical cutting accessories, such as the shaver discussed above, are commonly used in arthroscopic procedures, and allow for the resection of hard and soft bodily tissues, for example, those found within the knee, shoulder and other joints. In such a cutting accessory, the outer housing element defines a window or opening at the distal end, which window is defined by an edge of the wall of the outer housing element. The cutting element drive shaft at the distal end thereof also defines a window defined by an edge of the wall of the drive shaft, and when the drive shaft is disposed within the housing element, the drive shaft window is positioned adjacent the window of the housing element. As the drive shaft is moved relative to the housing element by the handpiece motor, the cutting edge of the drive shaft window and the opposed and facing cutting edge of the housing element window cause a cutting action which effectively severs tissue located within the housing element window and between the opposed cutting edges of the housing element and drive shaft. The configurations of these opposed edges allow for removal of particular tissue types, and a variety of different blade geometries are available to specifically address the type of cutting the accessory is to carry out. For example, providing the windows of both of the housing element and drive shaft with straight cutting edges is useful for making fine or detailed cuts and removing areas of hard tissue, such as bone. Alternatively, providing the distal ends of both the housing element and drive shaft with toothed or serrated cutting edges achieves a more aggressive cut and is useful for removal of soft fibrous tissue. Thus, a surgeon may often need to switch cutting accessories during a procedure in order to carry out the appropriate type or style of cut.

While the above-described surgical accessories have proven useful, when a change in cutting is desired, these accessories require the user to remove the accessory currently in use from the patient, to remove the accessory from the handpiece, install a different accessory onto the handpiece, and then reinsert the new accessory into the surgical site. Further, the known arrangements require the purchase of a multitude of accessories, which results in higher costs and a larger number of surgical accessories which must be present in the operating room in order to carry out the desired surgical procedure.

In order to obviate or at least minimize the above disadvantages of known arrangements, the surgical accessory according to the invention combines two types of cutting styles into one accessory. Specifically, in one embodiment, the two opposite sides of the cutting window of each of the outer housing element and the cutting element drive shaft have differently-configured cutting geometries, such that each window combines two different blade styles into one window. Further, the cutting geometries of the housing element window and the cutting element drive shaft window are reversed from one another, such that the accessory will perform one cutting style in one direction of rotation of the drive shaft, for example, a "straight-on-straight" cutting style wherein the opposed cutting edges of the drive shaft window and the housing element window are both straight, and such that the accessory will perform a different cutting style in an opposite direction of rotation of the drive shaft, for example, a "tooth-on-tooth" cutting style wherein the opposed cutting edges of the drive shaft window and the housing element window are both serrated or toothed. Providing this type of blade geometry on an accessory allows the surgeon to perform two different types of cutting without having to remove the accessory from the patient and then from the handpiece, thus saving time during a procedure and reducing equipment costs.

A further embodiment of the invention also combines two types of cutting styles into one accessory. In this embodiment, a surgical accessory is provided which includes a tubular housing element in which an inner cutting element is disposed for rotation relative thereto. Further, an outer sheath is provided over the housing and cutting elements, which sheath defines an opening or window at its distal end. The housing element in this embodiment is thus an intermediate component located radially between the sheath and the cutting element. The housing element defines therein a pair of windows located on opposite sides of the distal end thereof, wherein one of these windows is configured with a first cutting style, and the opposite window is configured with a second cutting style different from the first cutting style. The cutting element located within the housing element also defines a cutting window at its distal end, which window is configured with a cutting style which in one embodiment matches the cutting style of one of the housing element windows.

The outermost sheath is movable relative to the housing and cutting elements, and can be moved by the user into a first position wherein the sheath opening is circumferentially aligned with one of the cutting windows of the housing element, or a second position wherein the sheath opening is aligned with the other or opposite cutting window of the housing element. While the first embodiment discussed above allows the surgeon to select the type of cutting style by changing the direction of rotation of the cutting element drive shaft relative to the housing element, this embodiment allows the user to rotate the outer sheath relative to the housing and cutting elements to select the type of cutting style desired.

Alternatively, the two cutting edges of the cutting window of one or both of the cutting element or housing element may be provided with different geometries as in the first embodiment, and the cutting element can be actuated in different rotational directions to provide additional or alternative cutting-style options.

BRIEF DESCRIPTION OF THE DRAWINGS

FIG. 3 is an enlarged top and fragmentary view of the surgical accessory;

FIG. 4 is an enlarged longitudinal cross-sectional view of the surgical accessory of FIG. 3, as seen generally along line 4-4 in FIG. 3;

FIG. 9 is an enlarged, fragmentary and partial cross-sectional view of the distal end of the surgical accessory of FIG. 7;

FIG. 10 is an enlarged and fragmentary view of the distal end of the surgical accessory of FIG. 7, with the sheath rotated approximately 180 degrees from the position thereof in FIG. 9.

Figure 1:
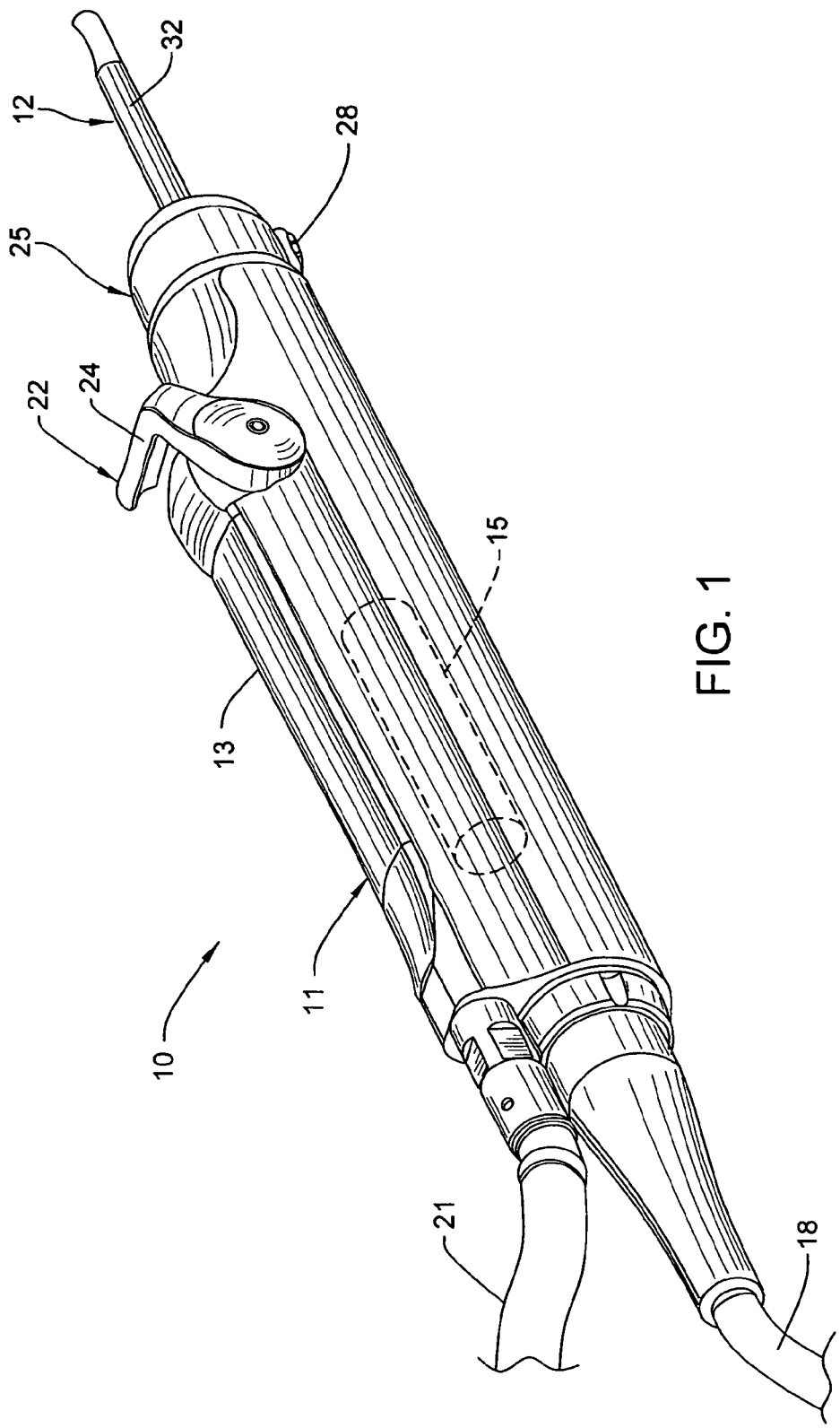
FIG. 1 is a perspective view of the surgical tool arrangement according to the invention, including a handpiece with a surgical accessory attached thereto.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. Said terminology will include the words specifically mentioned, derivatives thereof, and words of similar import.

DETAILED DESCRIPTION

Figure 2:
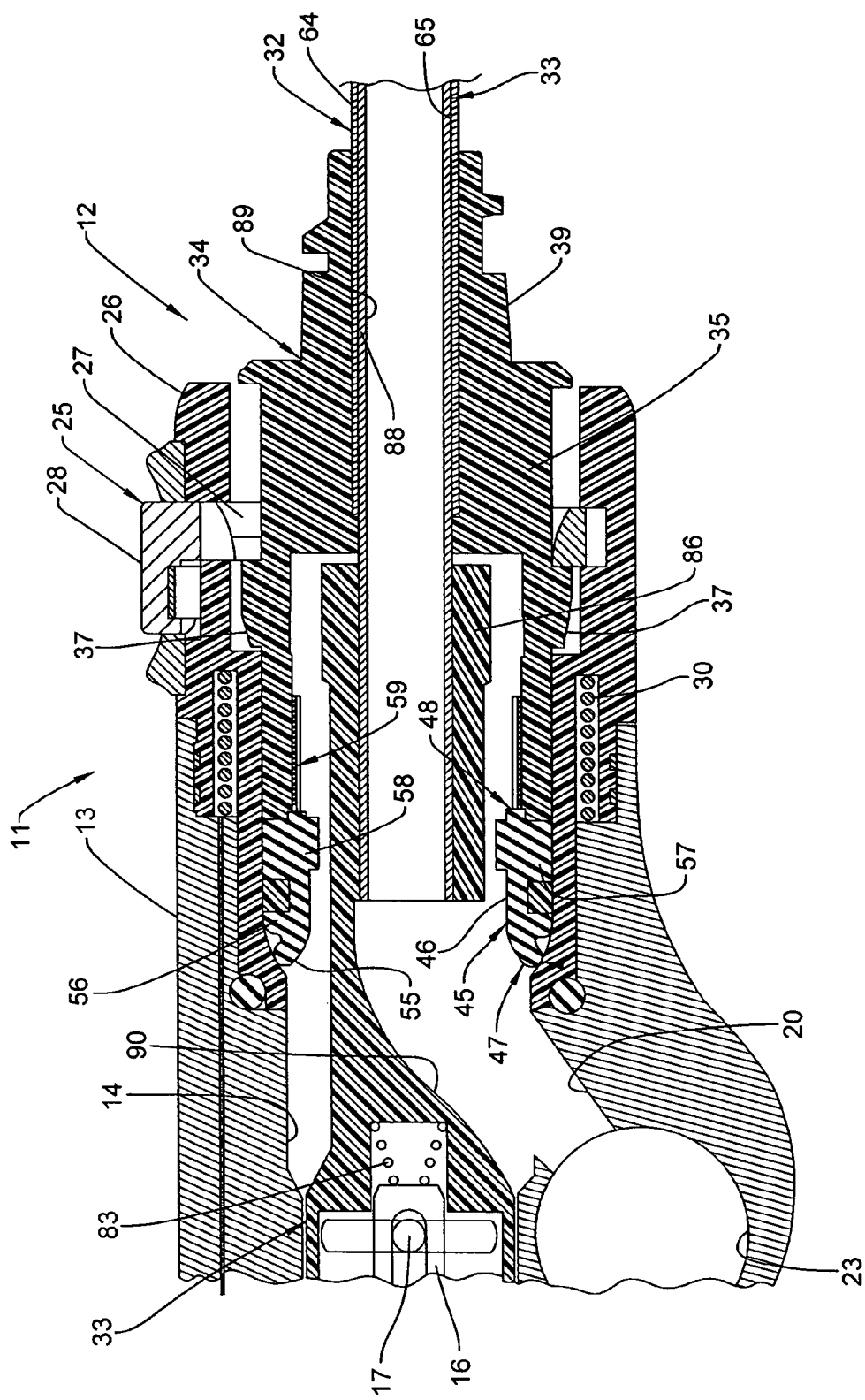
FIG. 2 is an enlarged, fragmentary longitudinal cross-sectional view of the handpiece of FIG. 1 with a surgical accessory attached thereto.

Referring to FIGS. 1 and 2, a surgical tool arrangement 10 according to the invention is illustrated. The arrangement 10 includes a handpiece 11, which at its distal end mounts thereon a surgical accessory 12.

Handpiece 11 is a commercially available surgical handpiece manufactured by the assignee hereof, under Model Nos. 375-704-500 and 375-701-500, and is accordingly only briefly described herein. Handpiece 11 includes an elongate outer housing 13 defining an elongate bore 14 therein. A motor 15 (shown diagrammatically only in FIG. 1) is disposed within housing bore 14. Motor 15 includes an output or drive shaft 16, which drive shaft 16 mounts a drive pin 17 at the distal end thereof. A power cable 18 is coupled to the proximal end of handpiece 11 for supplying power to motor 15.

Handpiece housing 13 defines therein an elongate suction bore (not shown) extending generally parallel to and sidewardly of housing bore 14. This suction bore communicates with a diagonally extending suction passage 20 defined in housing 13, which passage 20 provides communication between the distal end of housing bore 14 and the suction bore. Suction is drawn through the handpiece 11 by a suction pump (not shown), which is connected to the handpiece 11 via a suction tube 21. Suction flow through the handpiece 11 is regulated by an adjustable valve 22 having a valve stem (not shown) which is movably mounted in a valve bore 23 defined in housing 13. The valve 22 is adjusted by the user via a movable handle or arm 24 connected to the valve stem. The above handpiece suction arrangement is described in detail in U.S. Patent Application Publication No. 2003/0135151A1 published on Jul. 17, 2003, which is owned by the same assignee hereof and is hereby incorporated by reference herein.

The accessory 12 is removably attached to the distal end of the handpiece 11 by a coupling assembly 25 provided on the handpiece 11. Coupling assembly 25 includes a generally ring-shaped collet 26 secured to the distal end of the handpiece housing 13. A locking ring 27 is movably disposed in collet 26 and is biased to hold the accessory 12 within the housing bore 14 of handpiece 11. A release button 28 is provided on locking ring 27, and is used to release the locking ring 27 and allow removal of the accessory 12 from handpiece 11. Further, a coil 30 is provided in collet 26, which is used to facilitate inductive signal transfer to/from a radio-frequency identification device (RFID) disposed in the accessory 12 as discussed below.

Referring to FIGS. 2-4, the accessory 12 will now be described. Accessory 12 includes an outer cannula or tubular housing element 32 and a tubular cutting element 33 disposed within housing element 32. Housing element 32 includes a hub 34 which defines the proximal end thereof. Hub 34 is defined by a generally tubular base body 35, which defines therein a pair of generally rectangular and diametrically-opposed openings 36 adjacent the proximal end thereof. Base body 35 also has formed thereon a pair of outwardly-projecting, diametrically opposed and generally ramp-shaped ears 37 disposed distally of openings 36. Ears 37 cooperate with coupling assembly 25 of handpiece 11 to secure accessory 12 therein. Hub 34 has a distal end defined by a head 39 or nose of a reduced diameter as compared to base body 35. In the illustrated embodiment, a thread 40 extends about the circumference of head 39, which thread 40 may be used to attach an operating cannula (not shown) over housing element 32. Further, hub 34 defines therein a bore 41 which extends completely through the hub 34, and with which openings 36 of base body 35 communicate.

An annular seal 45 is disposed within the proximal end of bore 41 of hub 34. Seal 45 is constructed of a resilient elastomeric material, and is defined by a main section 46 and axially-spaced proximal and distal sections 47 and 48 disposed at respective opposite ends of the main section 46. Proximal section 47 defines thereon a pair of annular ribs 55 and 56, which are disposed in sealing engagement with an inner annular surface of collet 26 of handpiece 11 when accessory 12 is coupled thereto, as shown in FIG. 2. Distal section 48 defines thereon a pair of outwardly projecting and diametrically-opposed lock tabs 57 which engage within the respective openings 36 of hub 34 to secure the seal 45 to hub 34 and fix the axial position of seal 45 relative thereto. Distal section 48 additionally defines thereon a pair of inwardly projecting and diametrically-opposed stop tabs 58, which are generally radially aligned with the respective lock tabs 57. As shown in FIGS. 2 and 4, an RFID device 59 encapsulated within a ring structure is located within hub bore 41 distally from, and in axially-adjacent relationship with, the distal section 48 of seal 45.

The above-described coupling arrangement of handpiece 11 and the arrangement of the encapsulated RFID device 59 and coil 30 are disclosed in U.S. Patent Publication No. 2004/0220602A1 published on Nov. 4, 2004, which publication is owned by the same assignee hereof and is hereby incorporated by reference herein.

Figure 6:
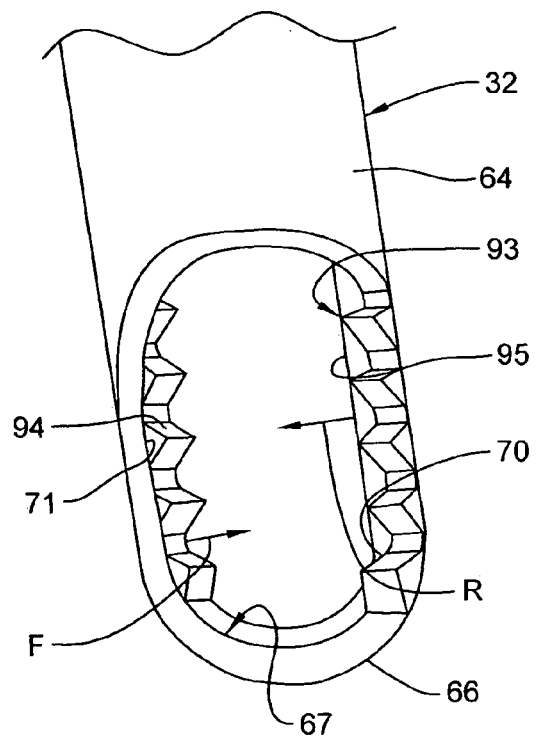
FIG. 6 is an enlarged and fragmentary view of the distal end of the surgical accessory of FIG. 3.
Figure 7:
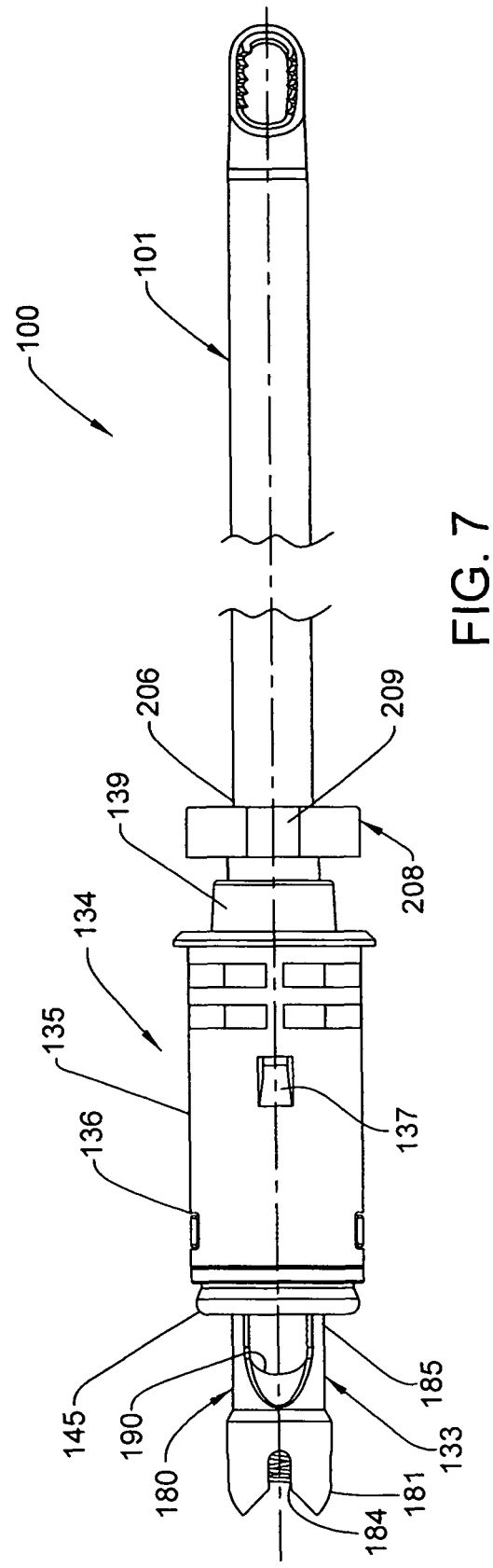
FIG. 7 is an enlarged top and fragmentary view of a further embodiment of a surgical accessory.
Figure 8:
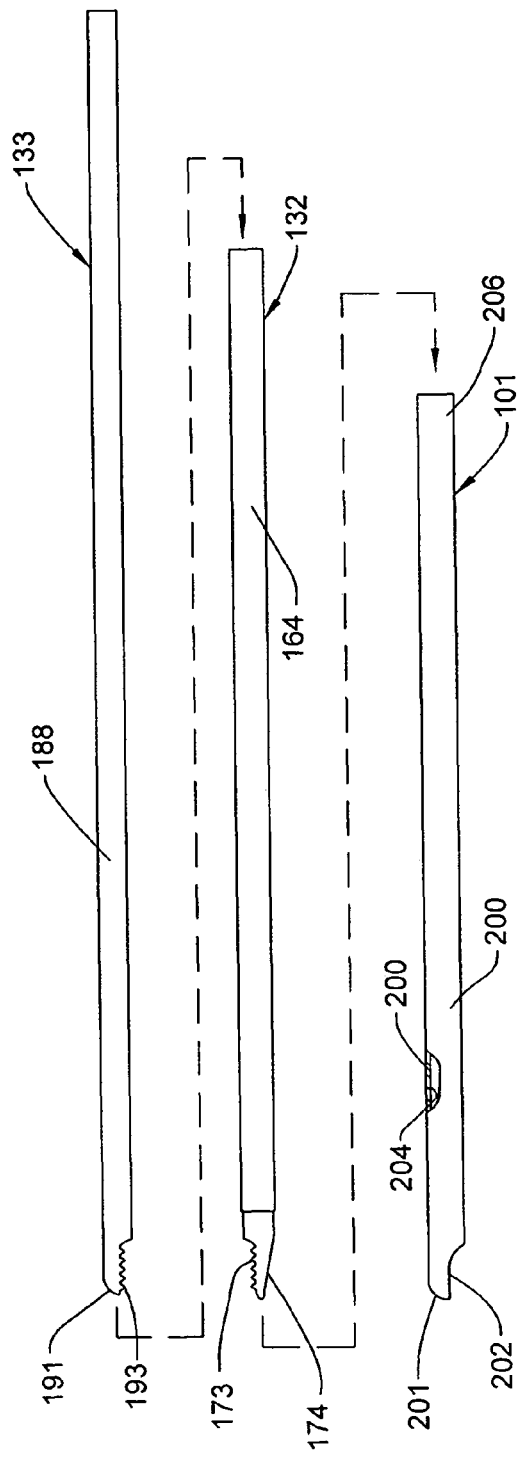
FIG. 8 is an exploded view of the sheath, housing element and drive shaft of the surgical accessory of FIG. 7.

Housing element 32 additionally includes an elongate housing tube 64 which projects distally from hub 34. More specifically, housing tube 64 has a proximal end which is fixedly mounted within the distal portion of bore 41 of hub 34. Housing tube 64 defines an elongate bore or conduit 65 therein, in which the cutting element 33 is disposed as discussed below. As best shown in FIGS. 6 and 7, housing tube 64 has a distal end 66 which is cut so as to define a window 67, which window 67 in the illustrated embodiment opens generally sidewardly of the tube 64, such that the distal end 66 is generally closed in the axial direction. The cutting of the housing tube 64 results in a ring-shaped edge of housing tube 64 which defines cutting window 67, which edge has circumferentially-spaced and opposed and generally longitudinally-extending sides 70 and 71. In the illustrated embodiment, one of these sides 70 is serrated so as to define a plurality of teeth thereon, and the other side 71 is non-toothed. In the illustrated embodiment, side 71 of window 67, as same extends longitudinally, has a generally straight or linear central region and curved end regions on opposite axial sides of the central region. However, it will be appreciated that side 71 may have a linear or straight configuration along its entire longitudinal extent.

Turning now to cutting element 33, same includes a hub 80 which defines the proximal end thereof. Hub 80 incorporates a motor-engaging drive element 81 defining a proximally opening bore 82 therein in which a coil spring 83 is located, and a slot 84 which extends transversely to the longitudinal axis of the cutting element 33. Hub 80 additionally includes a neck 85 which projects distally from drive element 81. Neck 85 terminates at a head 86 which has an enlarged outer diameter as compared to the remainder of neck 85. In this regard, the outer diameter of head 86 is slightly larger than the inward projection of the respective stop tabs 58 of seal 45. A bore 87 extends through neck 85 and head 86, in which an elongate and tubular drive shaft 88 is fixed. Drive shaft 88 defines therein a suction passage 89 which is in communication with a suction port 90 defined in neck 85, which suction port 90 is in turn in communication with suction passage 20 of handpiece 11.

Figure 5:
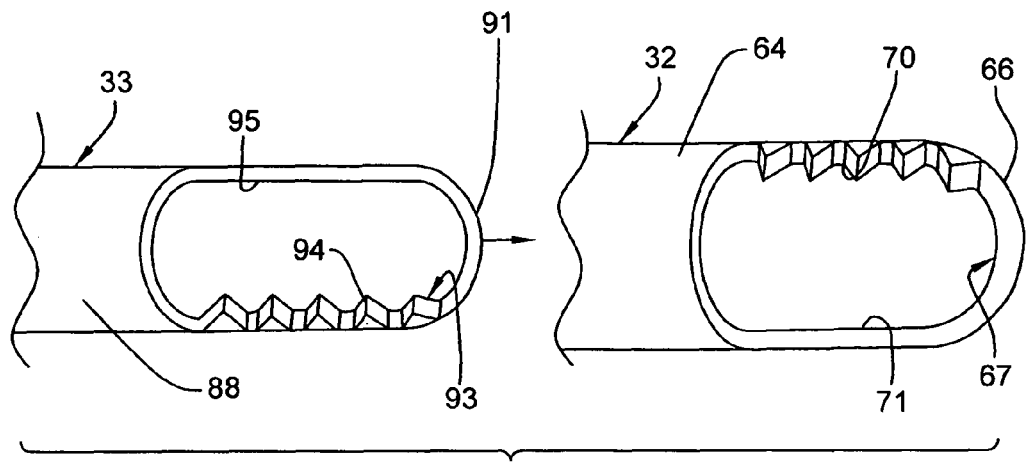
FIG. 5 is an enlarged, fragmentary and exploded view of distal ends of the housing element and drive shaft of the surgical accessory of FIG. 3.

Drive shaft 88 has a distal end 91 which is cut so as to define a window or opening 93. Window 93 in the illustrated embodiment opens generally sidewardly of the drive shaft 88, such that distal end 91 is generally closed in the axial direction. The cutting of drive shaft 88 results in a ring-shaped edge which defines cutting window 93. This ring-shaped edge of drive shaft 88 has circumferentially-spaced and opposed and generally longitudinally-extending sides 94 and 95. As best shown in FIGS. 5 and 6, side 94 of cutting window 93 in the illustrated embodiment is serrated or toothed, and the opposite side 95 of window 93 is non-toothed and generally straight.

The cutting element 33 is assembled to the outer tubular housing element 32 by inserting the distal end 91 of drive shaft 88 of cutting element 33 into bore 41 at the proximal end of hub 34. During this insertion, the enlarged head 86 of hub 80 expands the seal 45 and head 86 pushes past the stop tabs 58, at which point the seal 45 essentially resumes its original shape. The stop tabs 58, while allowing some axial displacement of cutting element 33 relative to housing element 32, prevent the cutting element 33 from detaching or falling out of the housing element 32 due to gravitational forces.

The assembled accessory 12 is secured to the handpiece 11 in a similar manner to that described in the '602 publication referenced above, and will accordingly be only briefly described here. Accessory 12 is attached to handpiece 11 by inserting the hubs 34 and 80 into the open distal end of collet 26. The ears 37 of hub 34 seat within collet 26, and the locking ring 27 serves to hold the accessory 12 within handpiece 11. The above securement of the accessory 12 to handpiece 11 causes the drive element 81 to engage the motor output shaft 16. More specifically, the drive pin 17 of output shaft 16 seats within slot 84 of drive element 81, such that the rotational movement of output shaft 16 is transferred to the cutting element 33. The spring 83 of drive element 81 biases the cutting element 33 forwardly or in the distal direction, so as to maintain the distal end 91 of cutting element 33 in bearing contact with the interior of the closed distal end 66 outer housing element 32.

In operation, the distal end of tool 10 is inserted into the surgical site. If desirable or necessary, the distal end of tool 10 can be inserted into the surgical site through a working portal defined by a conventional cannula or trocar (not shown). The cutting element 33 is controlled by a control unit (not shown) connected to handpiece cable 18, which control unit supplies electrical power to the motor 15 of handpiece 11 in order to actuate cutting element 33. Control unit also controls the mode of operation of cutting element 33, for example by controlling motor 15 so as to drive cutting element 33 in a forward or reverse direction, or in an oscillating manner. If cutting of tissue is desired, then motor 15 is activated so as to cause cutting element 33 to rotate within and relative to outer housing element 32. In this regard, it will be appreciated that the control unit may include appropriate control buttons so as to allow the surgeon or operator to select the desired accessory operations. These control functions of the cutting element 33 may alternatively be performed directly from the handpiece 11 which would then include the appropriate control buttons thereon. Alternatively, the control unit may be associated with a switch, either through a suitable cable or wirelessly, to allow the surgeon to operate the controls remotely. Such a switch may be a footswitch or a hand switch.

As shown in FIG. 6, with the cutting element 33 disposed within housing element 32 and the accessory 12 secured to handpiece 11 as described above, the toothed sides 94 and 70 of the respective cutting element window 93 and the housing tube window 67 are positioned on opposite longitudinal sides of the distal end of accessory 12, and the non-toothed sides 95 and 71 are positioned on opposite longitudinal sides of the distal end of accessory 12. This configuration allows the accessory 12 to perform one type of cutting or cutting style in the forward mode, and in the reverse mode the accessory 12 will perform a different type of cutting or cutting style. Further, in the oscillation mode, wherein the cutting element 33 oscillates rotationally relative to the outer housing element 32 about the longitudinal axis of the accessory 12, the accessory 12 will perform in both cutting styles. More specifically, when motor 15 is activated in a forward mode to cause cutting element 33 to rotate within and relative to outer housing element 32 (see arrow F in FIG. 6), the toothed side 94 of cutting element 33 is rotated towards and then past the toothed side 70 of outer housing element 32, which effectively cuts tissue located adjacent or within cutting window 67. This "tooth-on-tooth" mode can be utilized when a more aggressive tissue resection is desirable or necessary. When motor 15 is activated in a reverse mode (see arrow R in FIG. 6), the non-toothed side 95 of cutting element 33 is rotated towards and then past the non-toothed side 71 of outer housing element 32 to cut tissue located within/adjacent window 67. This "straight-on-straight" mode can be utilized when fine or detailed cutting is desirable or necessary.

If desirable or necessary, suction can be provided at the surgical site by manipulating valve 22 on handpiece 11 to draw surgical debris from the surgical site through windows 67 and 93, into drive shaft suction passage 89, into handpiece suction passage 20 and proximally through the handpiece 11 towards the suction pump.

The accessory 12 according to the invention thus allows the combination of two different blade styles into one tool or accessory, which is advantageous in that the surgeon need not remove the accessory 12 from the surgical site in order to change to a different cutting style, and can also reduce the costs associated with purchasing multiple blades. It will be appreciated that the accessory 12 can be customized for a particular surgical procedure, by providing two different blade styles which are particularly suited to a given surgical procedure. Thus, the "tooth-on-tooth" and "straight-on-straight" cutting styles of the outer housing element 32 and cutting element 33 are provided only as an example of one type of configuration of accessory 12, and other blade styles can be provided according to the invention.

Further, it will be appreciated that only one of the cutting windows 67 or 93 of the housing element 32 and the cutting element 33 may be provided with a window having differently-configured cutting edges, and the other element may be provided with a window having cutting edges of the same configuration. This arrangement will still allow two different cutting styles to be carried out upon rotation of the cutting element 33 in different directions relative to housing element 32. For example, the cutting window of cutting element 33 can be provided with both toothed and straight cutting edges and the window of the housing element 32 can be provided with two straight cutting edges. This arrangement will provide a "tooth-on-straight" cutting action in one direction of rotation of element 32, and a "straight-on-straight" cutting action in the opposite direction of rotation.

FIGS. 7-11 illustrate a further embodiment of the invention which will now be described. Components of this embodiment which are similar to or identical to components of the prior embodiment will include the same reference numbers as in the prior embodiment plus "100", and a detailed description of all components will accordingly not be provided. The surgical accessory 100 shown in FIGS. 7-11 generally includes an outermost sheath 101, a tubular housing element 132 and a tubular cutting element 133. Tubular cutting element 133 is disposed within housing element 132, and housing and cutting elements 132 and 133 are disposed within sheath 101, such that housing element 132 is located radially between sheath 101 and cutting element 133 and thus is an intermediate component.

Housing element 132 is fixed at its proximal end to a hub 134 which is substantially identical to hub 34 of the prior embodiment, and thus hub 134 will not be discussed in detail here except where same differs from hub 34. Housing element 132 includes a housing tube 164 defining an elongate bore or conduit 165 therein in which cutting element 133 is disposed. Housing tube 164 has a distal end 166 which is cut on opposite sides so as to define a pair of windows 173 and 174 which open into conduit 165. Windows 173 and 174, in the illustrated embodiment, are disposed approximately 180 degrees from one another along the outer circumference of housing tube 164. Windows 173 and 174 each open generally sidewardly of the housing tube 164, such that distal end 166 thereof is generally closed in the axial direction. Each of the cutting windows 173 and 174 is generally ring-shaped. Cutting window 173 has a pair of circumferentially-spaced, opposed and generally longitudinally-extending sides, both of which sides in the illustrated embodiment are serrated or toothed. The opposite cutting window 174 has a pair of circumferentially-spaced, opposed and generally longitudinally-extending sides, each of which sides in the illustrated embodiment is non-toothed or generally straight.

Cutting element 133 is fixed at its proximal end to a hub 180 which is identical to hub 80 of accessory 12 described above. Cutting element 133 includes a tubular drive shaft 188, the proximal end of which is mounted within the bore of hub 180. Drive shaft 188 defines therein a suction passage 189 in communication with suction port 190 of hub 180 and suction passage 20 of handpiece 11. Cutting element 133 has a distal end 191 which defines a window or opening 193 therein. Window 193 opens generally sidewardly of drive shaft 188 such that distal end 191 is closed in the axial direction. Cutting window 193 is generally ring-shaped and has a pair of opposed and generally longitudinally-extending sides, both of which sides in the illustrated embodiment are serrated or toothed.

Turning now to outermost sheath 101, same is defined by a tubular wall 200 having a distal end 201. Distal end 201 is cut so as to define a window 202 therein which opens generally sidewardly of wall 200 such that distal end 201 is closed in the axial direction. Further, tubular wall 200 of sheath 101 defines an elongate conduit 204 therein in which housing and cutting elements 132 and 133 are disposed, and thus the inner diameter of conduit 204 is of a dimension slightly larger than an outer diameter of housing tube 164 of housing element 132.

As shown in FIG. 7, sheath 101 has a proximal end 206 on which an adjustment knob 208 is fixed. In one embodiment, knob 208 is annular in shape and opens proximally so as to fit over nose 139 of hub 134 of housing element 132, and opens distally so as to mount therein the proximal end 206 of sheath 101. In this regard, knob 208 is fixed to sheath 101, but is rotatably movable relative to hub 134 between a first position in which sheath window 202 is circumferentially and axially aligned with window 173 of housing element 132, and a second position in which sheath window 202 is circumferentially and axially aligned with the opposite window 174 of housing element 132. These positions, located approximately 180 degrees from one another, may be achieved by providing stops in appropriate positions on nose 139 of hub 134. Knob 208 may be provided with one or more adjustment levers 209 which project outwardly from knob 208 and aid the user in moving the knob 208 into the desired rotational position.

The cutting element 133 is assembled to housing element 132 in the same manner as discussed above relative to accessory 12, and thus such assembly will not be repeated here. The distal end 166 of housing element 132 is inserted into the proximal end of adjustment knob 208 and into sheath 101, and sheath 101 is moved rearwardly relative to housing element 132 until knob 208 seats over and onto nose 139 of hub 134. Sheath 101 is retained on hub 134 in the axial direction via friction or other suitable retaining structures. The assembled accessory 100 is secured to the handpiece 11 in the same manner that accessory 12 is secured to handpiece 11.

In operation, the sheath 101 is adjusted to the correct rotational position relative to outer housing element 132 using knob 208 so as to expose appropriate window 173 or 174 of housing element 132 depending upon what type of cutting action is desirable or necessary. The distal end of accessory 12 is inserted into the surgical site, and the handpiece motor 15 activated so as to drive cutting element 133 in a forward, reverse or oscillating mode. FIG. 9 illustrates the distal end of the accessory 100 when the sheath 101 is positioned so that the toothed cutting window 173 of housing element 132 is exposed, which when the cutting element 133 is rotated by motor 15 in the forward, reverse or oscillating mode will provide a "tooth-on-tooth" cutting action, for example, to achieve an aggressive cutting action. With the sheath 101 in this position, one toothed side of the cutting window 193 of cutting element 133 will rotate towards and past the opposed toothed side of cutting window 173 of housing element 132, which cuts tissue located adjacent/within cutting window 173. FIG. 10 illustrates the distal end of the accessory 100 when the sheath 101 is positioned so that the non-toothed cutting window 174 is exposed, which when the cutting element 133 is rotated in the forward, reverse or oscillating mode will provide a "tooth-on-straight" cutting action, for example to make a less aggressive cut than a "tooth-on-tooth" cutting action.

The accessory 100, as in the first embodiment, thus allows the combination of two different blade styles into one tool or accessory, which avoids the surgeon having to remove the accessory 100 from the surgical site and from the handpiece 11 to switch cutting styles. Accessory 100 can also help to reduce costs in that not as many blades need be purchased. It will be appreciated that the accessory 100 can be customized for particular surgical procedures, and that the blade configurations provided at the cutting windows may vary from what is depicted herein.

Figure 11:
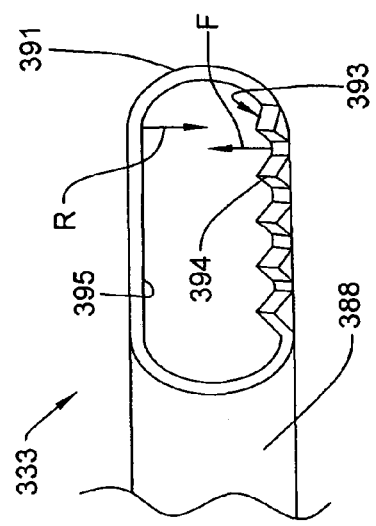
FIG. 11 is an enlarged and fragmentary view of the distal end of a further embodiment of a cutting element which may be utilized with the accessory of FIG. 7.

FIG. 11 illustrates an alternative embodiment of the cutting element 133 described above, which cutting element 333 can be provided in place of cutting element 133. Specifically, cutting element 333 in this embodiment includes a tubular drive shaft 388 having a distal end 391. Distal end 391 defines a window or opening 393 therein which opens generally sidewardly of drive shaft 388 such that distal end 391 is closed in the axial direction. Cutting window 393 is generally ring-shaped and has a pair of opposed and generally longitudinally-extending sides, one of which sides 394 is serrated or toothed, and the other of which sides 395 is generally straight.

In this embodiment, when sheath 101 is positioned so as to expose toothed cutting window 173 of housing element 132, cutting element 333 when rotated by motor 15 in the forward direction (shown by arrow "F" in FIG. 11) will provide an aggressive "tooth-on-tooth" cutting action via the cooperation of toothed cutting edge 394 of cutting element 333 and toothed window 173 of housing element 132, and when rotated by motor 15 in the reverse direction (shown by arrow "R" in FIG. 11) will provide a less aggressive "straight-on-tooth" cutting action via the cooperation of straight cutting edge 395 and toothed window 173. When sheath 101 is positioned so as to expose straight cutting window 174 of housing element 132, cutting element 333 when rotated in the forward direction F will provide a "straight-on-tooth" cutting action via cooperation of toothed cutting edge 394 and window 174, and when rotated in the reverse direction R will provide a "straight-on-straight" cutting action via cooperation of straight cutting edge 395 and window 174 and from the handpiece for a more precise cut.

Thus, the above embodiment which utilizes a cutting window 393 which incorporates two different cutting styles in a single cutting window, provides the surgeon with two different cutting styles in each rotational position of the sheath 101. This embodiment also avoids the surgeon having to remove the accessory from the surgical site and then from the handpiece 11 in order to change to a different cutting style, and can also reduce the number of accessories which must be purchased and which must be present during a surgical procedure.

It will be appreciated that the housing element 132 may be configured with a cutting window or windows similar to that shown above relative to cutting element 333 (in addition to or in place of cutting element 333) which may provide additional or alternative cutting styles than those discussed above.

Although particular preferred embodiments of the invention are disclosed in detail for illustrative purposes, it will be recognized that variations or modifications of the disclosed apparatus, including the rearrangement of parts, lie within the scope of the present invention.

What is claimed is:

1. A surgical cutting accessory configured for being attached to and driven by a powered surgical handpiece, said accessory comprising:
a cutting element assembly including a hub defining a proximal end of said cutting element assembly and configured for cooperation with a drive member of a powered surgical handpiece, and an elongate drive shaft having a proximal end connected to said hub and a distal end defining a first cutting window therein, said first cutting window having a pair of spaced-apart first and second cutting edges; and
an outer housing assembly including a hub defining a proximal end of said outer housing assembly and configured for cooperation with a coupling arrangement provided on a powered surgical handpiece, an elongate and generally tubular housing element in which said drive shaft is disposed for movement relative to said housing element, said housing element having a proximal end connected to said housing assembly hub and a distal end defining a second cutting window therein disposed adjacent said first cutting window of said drive shaft, said second cutting window having a pair of spaced-apart first and second cutting edges, wherein one of said first cutting edge and said second cutting edge of one of said first and second cutting windows has a cutting profile different from the other said cutting edge of said one cutting window;
wherein said cutting profile of said one cutting edge of said one cutting window is toothed and said cutting profile of said other cutting edge of said one cutting window is generally straight.

2. The cutting accessory of claim 1, wherein said accessory defines a generally centrally oriented longitudinal axis, said first and second cutting edges of said first cutting window extend generally longitudinally along said distal end of said drive shaft and are spaced circumferentially from one another, and said first and second cutting edges of said second cutting window extend generally longitudinally along said distal end of said housing element and are spaced circumferentially from one another.

3. The cutting accessory of claim 2, wherein said drive shaft of said cutting element is rotatably movable relative to and within said housing element in a first direction of rotation to move said first cutting edge of said first cutting window towards said second cutting edge of said second cutting window to achieve a first cutting action, and in a second direction of rotation opposite to said first direction of rotation to move said second cutting edge of said first cutting window towards said first cutting edge of said second cutting window to achieve a second cutting action different from said first cutting action.

4. The cutting accessory of claim 1, wherein one of said cutting edges of the other cutting window has a toothed cutting profile and the other of said cutting edges of said other cutting window has a generally straight cutting profile, said drive shaft of said cutting element is rotatably movable relative to and within said housing element in a first direction of rotation to move said one cutting edge of said one cutting window having said toothed cutting profile towards said one cutting edge of said other cutting window having said toothed cutting profile to achieve a first cutting action, and in a second direction of rotation opposite to said first direction of rotation to move said other cutting edge of said one cutting window having said generally straight cutting profile towards said other cutting edge of said other cutting window having said generally straight cutting profile to achieve a second cutting action different from said first cutting action.

5. The cutting accessory of claim 1, wherein said one cutting window is disposed on said drive shaft.

6. The cutting accessory of claim 1, wherein said first cutting edge of said first cutting window has a first cutting profile and said second cutting edge of said first cutting window has a second cutting profile different from said first cutting profile, said first cutting edge of said second cutting window having a first cutting profile which matches said second cutting profile of said second cutting edge of said first cutting window and said second cutting edge of said second cutting window having a second cutting profile which matches said first cutting profile of said first cutting edge of said first cutting window.

7. The cutting accessory of claim 6, wherein said drive shaft of said cutting element is rotatably movable relative to and within said housing element in a first direction of rotation to move said first cutting edge of said first cutting window towards said second cutting edge of said second cutting window to achieve a first cutting action, and in a second direction of rotation opposite to said first direction of rotation to move said second cutting edge of said first cutting window towards said first cutting edge of said second cutting window to achieve a second cutting action different from said first cutting action.

8. The accessory of claim 7, wherein said first cutting edge of said first cutting window and said second cutting edge of said second cutting window are toothed, and said second cutting edge of said first cutting window and said first cutting edge of said second cutting window are generally straight.

9. A surgical cutting accessory configured for attachment to a surgical handpiece, said accessory comprising:
a cutting element having a proximal end and a distal end defining a first and second spaced-apart cutting edges thereon; and
an outer housing element in which said cutting element is disposed for movement relative to said housing element, said housing element having a proximal end and a distal end defining first and second spaced-apart cutting edges thereon disposed adjacent said cutting edges of said cutting element, wherein one of said first cutting edge and said second cutting edge of one of said elements has a cutting profile different from a cutting profile of the other said cutting edge of said one element;
wherein said cutting profile of said one cutting edge of said one element is toothed, and said cutting profile of said other cutting edge of said one element is generally straight.

10. The accessory of claim 9, wherein each of said cutting element and said housing element is tubular and defines at said distal end thereof a window which opens into an interior of said element, said window having opposite sides respectively defining the respective said first and second cutting edges thereon.

11. The accessory of claim 10, wherein said accessory defines a generally centrally oriented longitudinal axis, said window of each said element opens sidewardly in a direction transverse to the accessory axis, and said first and second cutting edges of each said window are spaced circumferentially from one another.

12. The accessory of claim 10, wherein said accessory defines a generally centrally oriented longitudinal axis, said window of said cutting element is a first window and said window of said housing element is a second window, said cutting element mounts a hub on said proximal end thereof configured for being rotatably driven by a drive member of a powered surgical handpiece and said housing element mounts a hub on said proximal end thereof configured for attachment to a powered surgical handpiece, said cutting element being rotatably movable relative to and within said housing element in a first direction of rotation to move said first cutting edge of said first cutting window towards said second cutting edge of said second cutting window to achieve a first cutting action, and in a second direction of rotation opposite to said first direction of rotation to move said second cutting edge of said first cutting window towards said first cutting edge of said second cutting window to achieve a second cutting action different from said first cutting action.

13. The accessory of claim 12, wherein said first cutting edge of said first cutting window has a first cutting profile and said second cutting edge of said first cutting window has a second cutting profile different from said first cutting profile, said first cutting edge of said second cutting window having a first cutting profile which matches said second cutting profile of said second cutting edge of said first cutting window and said second cutting edge of said second cutting window having a second cutting profile which matches said first cutting profile of said first cutting edge of said first cutting window.

14. A surgical tool assembly comprising:
a powered handpiece including a housing and a motor disposed therein, said motor having an output shaft and said housing mounting a coupling arrangement adjacent a distal end thereof; and
an accessory comprising:
a cutting element assembly having a hub at a proximal end thereof which engages with said output shaft of said handpiece, and an elongate drive shaft having a proximal end connected to said hub and a distal end defining a first cutting window therein, said first cutting window having a pair of spaced-apart first and second cutting edges; and
an outer housing assembly having a hub at a proximal end thereof which engages with said coupling arrangement of said handpiece, an elongate and generally tubular housing element in which said drive shaft is disposed for movement relative to said housing element, said housing element having a proximal end connected to said housing assembly hub and a distal end defining a second cutting window therein disposed adjacent said first cutting window of said drive shaft, said second cutting window having a pair of spaced-apart first and second cutting edges, wherein one of said first cutting edge and said second cutting edge of one of said first and second cutting windows has a cutting profile different from the other said cutting edge of said one cutting window;
wherein said cutting profile of said one cutting edge of said one cutting window is toothed and said cutting profile of said other cutting edge of said one cutting window is generally straight.

15. The surgical tool assembly of claim 14, wherein said first cutting edge of said first cutting window has a first cutting profile and said second cutting edge of said first cutting window has a second cutting profile different from said first cutting profile, said first cutting edge of said second cutting window having a first cutting profile which matches said second cutting profile of said second cutting edge of said first cutting window and said second cutting edge of said second cutting window having a second cutting profile which matches said first cutting profile of said first cutting edge of said first cutting window.

16. The surgical tool assembly of claim 15, wherein said drive shaft of said cutting element is rotatably movable relative to and within said housing element in a first direction of rotation to move said first cutting edge of said first cutting window towards said second cutting edge of said second cutting window to achieve a first cutting action, and in a second direction of rotation opposite to said first direction of rotation to move said second cutting edge of said first cutting window towards said first cutting edge of said second cutting window to achieve a second cutting action different from said first cutting action.

17. The surgical tool assembly of claim 14, wherein said drive shaft of said cutting element is rotatably movable relative to and within said housing element in a first direction of rotation to move said first cutting edge of said first cutting window towards said second cutting edge of said second cutting window to achieve a first cutting action, and in a second direction of rotation opposite to said first direction of rotation to move said second cutting edge of said first cutting window towards said first cutting edge of said second cutting window to achieve a second cutting action different from said first cutting action.

* * * * *